US00PP22489P2

(12) United States Plant Patent
Egger

(10) Patent No.: US PP22,489 P2
(45) Date of Patent: Feb. 7, 2012

(54) ***KNIPHOFIA* PLANT NAMED 'CREAMSICLE'**

(50) Latin Name: ***Kniphofia* spp.**
Varietal Denomination: Creamsicle

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/066,143

(22) Filed: Apr. 6, 2011

(51) Int. Cl.
*A01H 5/00* (2006.01)

(52) U.S. Cl. ..... Plt./443

(58) Field of Classification Search ..... Plt./443
See application file for complete search history.

*Primary Examiner* — June Hwu
*Assistant Examiner* — Louanne Krawczewicz Myers
(74) *Attorney, Agent, or Firm* — Klarquist Sparkman, LLP

(57) ABSTRACT

A new and distinct *Kniphofia* plant characterized by its very long, repeat blooming, compact habit with multiple crowns, narrow, grassy leaves, creamy red orange flowers, and excellent vigor.

1 Drawing Sheet

Botanical denomination: *Kniphofia* spp.
Cultivar designation: 'Creamsicle'.

BACKGROUND OF THE INVENTION

The present invention relates to a new and distinct *Kniphofia,* and given the cultivar name is 'Creamsicle'. *Kniphofia* is in the family Asphodelaceae. 'Creamsicle' is a hybrid resulting from a planned breeding program to produce compact, reblooming *Kniphofia.* The cross was made using the following proprietary, unreleased, unpatented plants: *Kniphofia* K9-2, as the seed parent, and *Kniphofia* K9-1, as the pollen parent. It was selected for best habit, flower color, reblooming, and crown count from many seedlings of the cross in Canby, Oreg.

Compared to the unpatented parent plants K9-1 and K9-2, the new variety has a more compact habit than its parents.

Compared to *Kniphofia* 'Bressingham Comet' (an unpatented plant), the new cultivar is more free flowering, shorter, and with creamsicle orange inflorescences rather than bicolor red orange and yellow.

Compared to *Kniphofia* 'Papaya Popsicle', U.S. Plant Pat. Ser. No. 13/066,135 applied for concurrently, the new cultivar has inflorescences that are smaller and creamsicle orange rather than bicolor red orange and yellow.

SUMMARY OF THE INVENTION

The new cultivar is unique and characterized by:

1. very early blooming (flowers the first year in 30 cell plugs)
2. repeat blooming from June through September in Canby, Oreg.
3. compact habit with multiple crowns
4. narrow, grassy leaves
5. creamy red orange flower color
6. excellent vigor This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a plant of a one-year-old *Kniphofia* 'Creamsicle' in the ground in the trial field in August in Canby, Oreg.

DETAILED PLANT DESCRIPTION

The following is a detailed description of the new *Kniphofia* cultivar based on observations one gallon size, nine-month-old specimens grown from tissue culture, grown outside in part sun in Canby, Oreg. The color descriptions are all based on The Royal Horticultural Society Colour Chart, 5$^{th}$ edition.

Plant:
- *Type.*—Rhizomatous herbaceous perennial.
- *Hardiness.*—USDA Zones 6 to 9.
- *Size.*—Grows to 34 cm wide and 36 cm tall from the top of the soil to the top of the foliage.
- *Crown #.*—About 14.
- *Form.*—Upright and clumping.

Leaf:
- *Type.*—Simple.
- *Shape.*—Strap-like.
- *Arrangement.*—Basal rosette.
- *Blade size.*—Grows to 45 cm long and 9 mm wide.
- *Margins.*—Entire.
- *Apex.*—Acuminate.
- *Base.*—Clasping.
- *Surface texture.*—Glabrous on both surfaces.
- *Venation.*—Parallel.
- *Color.*—Top and bottom side Green 137A.

Inflorescence:
- *Type.*—Spike-like scapose raceme.
- *Number of flowers per raceme.*—About 60.

*Inflorescence.*—13 cm long and 5 cm wide.

*Peduncle description.*—Grows to 44 cm long and 6 mm wide, glabrous, Yellow Green 146B.

*Pedicel description.*—1.5 mm long, glabrous, Yellow Green 152A.

*Bloom time.*—June through September in Canby, Oreg.

*Lastingness.*—An inflorescence lasts for 2 to 4 weeks depending on the temperature.

Flower bud:

*Size.*—20 mm long and 5 mm wide.

*Shape.*—Cylindrical.

*Surface texture.*—Glabrous.

*Color.*—Orange Red 31 B on top and Orange 25D on the bottom, tip and veins Orange Red 34B, bottom 2 mm Green Yellow IC.

Flower:

*Type.*—Actinomorphic.

*Shape.*—Cylindrical and tubular.

*Size.*—Grows to 23 mm deep and 11 mm wide.

*Surface texture.*—Glabrous inside and outside.

*Corolla description.*—6 lobed fused tepals, 22 mm long and 11 mm wide, tube 20 mm long and 7 mm wide, lobes reflex, each 3 mm wide and 3 mm long, shape ovate, margin entire, tip 2 notched and acute; outside color Orange Red 34C lightening to Orange 24C on the bottom with veins Orange Red 34B, inside color Orange Red 31C with veins Orange Red 34B.

*Pistil description.*—One, 25 mm long, ovary 3 mm long 2.5 mm wide, Yellow Green 152C, style 22 mm long, Greyed Yellow 161B, stigma Greyed Yellow 161D.

*Stamen.*—6, 24 mm long, filaments 23 mm long, and White 155A, anthers 1 mm long and Greyed Orange 163A, pollen Yellow 11B.

*Fragrance.*—None.

Fruit and seed—none seen:

Pest and diseases: Pests and diseases are infrequent on *Kniphofia* spp. No problems have been observed on this plant grown under commercial conditions in Canby, Oreg.

I claim:

1. A new and distinct *Kniphofia* plant as herein shown and described.

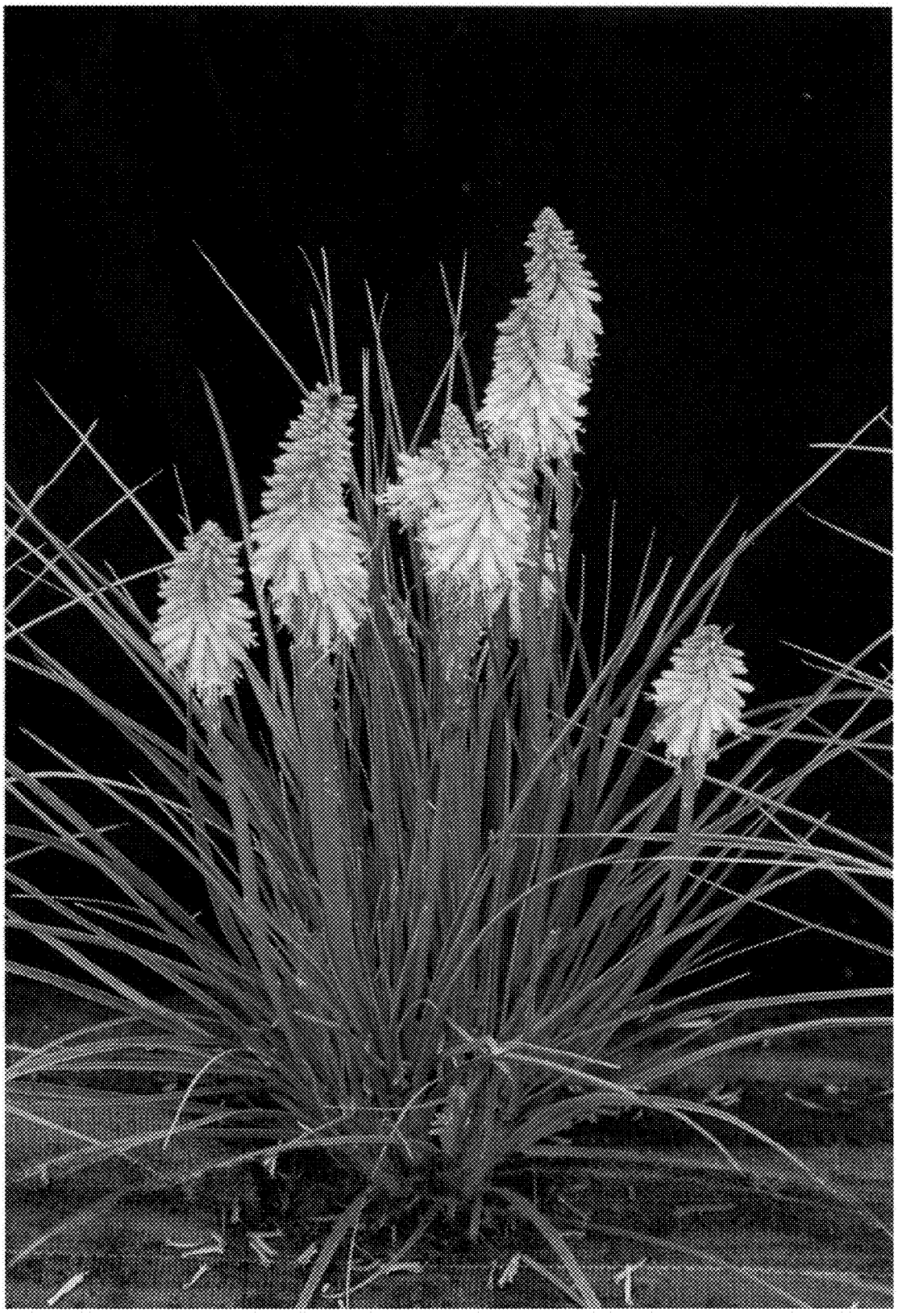

* * * * *